United States Patent
da Costa Pereira

(10) Patent No.: US 9,526,690 B2
(45) Date of Patent: Dec. 27, 2016

(54) DEPIGMENTING COSMETIC COMPOSITION AND ITS PREPARATION PROCESS

(71) Applicant: Hypermarcas SA, Sao Paulo (BR)

(72) Inventor: Andreia Feital da Costa Pereira, Jacarepagua (BR)

(73) Assignee: Hypermarcas SA, Sao Paulo (BR)

( * ) Notice: Subject to any disclaimer, the term of this patent is extended or adjusted under 35 U.S.C. 154(b) by 714 days.

(21) Appl. No.: 13/803,161

(22) Filed: Mar. 14, 2013

(65) Prior Publication Data
US 2013/0266675 A1 Oct. 10, 2013

Related U.S. Application Data

(60) Provisional application No. 61/619,239, filed on Apr. 2, 2012.

(51) Int. Cl.
| | | |
|---|---|---|
| *A61K 8/97* | (2006.01) | |
| *A61K 8/49* | (2006.01) | |
| *A61K 8/44* | (2006.01) | |
| *A61K 8/60* | (2006.01) | |
| *A61Q 19/02* | (2006.01) | |

(52) U.S. Cl.
CPC . *A61K 8/97* (2013.01); *A61K 8/44* (2013.01); *A61K 8/498* (2013.01); *A61K 8/602* (2013.01); *A61Q 19/02* (2013.01)

(58) Field of Classification Search
None
See application file for complete search history.

(56) References Cited

U.S. PATENT DOCUMENTS

| | | | | |
|---|---|---|---|---|
| 2005/0118119 A1* | 6/2005 | Stoltz | | A61K 8/44 424/62 |
| 2009/0263340 A1* | 10/2009 | Ille-Boehler | | A61K 8/368 424/62 |

FOREIGN PATENT DOCUMENTS

| | | | |
|---|---|---|---|
| JP | 08325130 A | * | 12/1996 |
| KR | 2003071893 A | * | 9/2003 |

* cited by examiner

*Primary Examiner* — Amy L Clark
(74) *Attorney, Agent, or Firm* — Wolf, Greenfield & Sacks, P.C.

(57) ABSTRACT

This invention generally provides depigmenting cosmetic compositions comprising four active whitening ingredients: undecylenoyl phenylalanine, alpha-arbutin, kojic acid and *brassica napus* extract, and methods for forming the same.

14 Claims, No Drawings

DEPIGMENTING COSMETIC COMPOSITION AND ITS PREPARATION PROCESS

RELATED APPLICATIONS

The present application claims priority under 35 U.S.C. §119(e) to U.S. provisional application, U.S. Ser. No. 61/619,239, filed Apr. 2, 2012, entitled "DEPIGMENTING COSMETIC COMPOSITION AND ITS PREPARATION PROCESS," incorporated herein by reference in its entirety for all purposes.

FIELD OF THE INVENTION

This invention regards a de-pigmenting composition for cosmetic application, comprehending four active ingredients: Undecylenoyl phenylalanine, alpha-arbutin, kojic acid and *brassica napus* extract, and its manufacturing process.

DESCRIPTION OF RELATED ARTS

Melanogenesis is physiological process resulting of the synthesis of the melanin pigments, and is characterized, in summary, by the production process and subsequent distribution of melanin by melanocytes. Melanocytes have complex organelles called melanosomes, containing various enzymes, among which tyrosinase, which measured melanin formation through tyrosine. Tyrosinase, also called polyphenol oxidase, is a copper-containing multifunctional enzyme, is the key enzyme in the first stage of melanogenesis cascade, catalyzing the conversion of L-tyrosine in L-dopaquinone (Ito, S. Wakamatsu K., and Ozeki, H. Chemical analysis of melanins and its application to the study of the regulation of melanogenesis. Pigment Cell Res. 2000: 13 Suppl. 8. 103-9). In addition to tyrosinase and other enzymes such as TRP-1 (Tyrosinase-related protein-1) or DHICA (5,6-dihydroxiindol-2-carboxylic acid oxidase) and TRP-2 (Tyrosinase-related protein-2) or dopachrome tautomerase, non-enzymatic factors interfere in the melanin synthesis, such as pH, concentration thiols and metallic ions or oligoelements, such as calcium (Hearing. V. J. The melanosome: the perfect model for cellular response to the environment Pigment Cell Res. 2000; 13 Suppl. 8, 23-4). Melanin is also originated in tyrosine oxidation by the enzyme tyrosinase to dihydroxyphenylalanine (DOPA) inside specialized cells called melanocytes. In this process, two types of melanin are synthetized in the melanosomes: eumelanin—a dark brown insoluble polymer—and pheomelanin—a gray-red polymer soluble in alkaline medium. After the production, melanin, within the melanosomes, is transferred to the adjacent keratinocytes through the dendrites present in the melanocytes, where it shall be transported and degraded. This melanin transference is mediated by the adenilcyclase and may occur through three different mechanisms: Cytophagocytosis process of the dendritic end of the melanocyte by the keratinocyte; direct migration of melanosomes of the cytoplasm to the keratinocyte and; release of the melanosomes in the extracellular space and its incorporation to the keratinocytes. Thus, skin pigmentation depends on the chemical nature of melanin, of the tyrosinase activity in the melanocytes, and the transference of melanin in the neighbor keratinocytes. UVA rays promote the oxidation of uncolored precursors of melanin, through a direct and immediate pigmentation without erythema. UVB rays promote indirect pigmentation, due to an increase in active melanocytes and stimulation of tyrosinase, causing actinic erythema.

Normally after 72 hours, late reactions are evidenced through the neosynthesis of melanin and melanosomes. Increased melanin production due to the direct or indirect stimulation is a defensive reaction of skin in order to protect against solar aggressions. After irradiation, the melanosomes regroup around the nucleus in order to protect the cell's genetic material and thus, in addition to promoting the skin and hair coloring, melanin promotes photo protection, acting as a sun filter, diffracting or reflecting solar radiation. Disorders in melanin amount and distribution may cause a series of diseases related to cutaneous dischromia. Abnormal melanin accumulation is responsible for various hyperpigmentation processes, such as melisma, ephelides, post-inflammation hyperchromias and solar melanoses. Hyperpigmentation is a disorder caused by exaggerated melanin production. Factors such as excessive solar exposure, aging, hormone changes, inflammation, allergies, among others, may cause an unbalance in the melanin production and distribution process, resulting in skin stains. Depigmenting cosmetic products are preparations used to reduce hyperchromia. Conceptually, depigmenting products are drugs or cosmetic actives which, upon inhibiting a melanin biosynthesis route, or acting directly on it, cause a clearing action of the skin area where they were applied. Hydroquinone has been the gold standard for hyperpigmentation treatment for over 40 years. Hydroquinone has a chemical structure similar to the precursor of melanin, and performs inhibiting tyrosine oxidation in 3,4-di-hydroxiphenylalanine. It acts on tyrosinase, causing its inhibition. Its application as a depigmenting substance may be broadly observed in various patent requests, such as:

U.S. Pat. No. 3,856,934, deposited on Jan. 22, 1973, which describes a skin-depigmenting cosmetic composition comprehending a mixture of hydroquinone, retinoic acid and corticosteroid.

PI 9200237-4, deposited on Jan. 21, 1992, which describes a formulation to prevent dark stains on the epidermis;

PI 9307824-2, deposited on Mar. 10, 1993, which describes a composition for skin whitening;

PI 0314882-3, deposited on Oct. 24, 2003, describing a composition for the treatment of hyperpigmented skin conditions, such as melasma;

CN1256912, deposited on Dec. 17, 1998, which describes a skin-whitening cosmetic composition containing hydroquinone; and U.S. Pat. No. 8,003,824, deposited on Mar. 6, 2009, describing a preparation of compounds with hydroquinone for cosmetic and pharmaceutical preparations for the prevention of biologic degradations caused by free radicals.

Hydroquinone is derived from phenol, being cytotoxic, mainly when used in high doses and for prolonged periods. Some of the other possible mechanisms of action of the drug are destruction of melanocytes, degradation of melanosomes and DNA and RNA synthesis inhibition. However, the diversity of adverse events caused thereby, such as irritating contact and allergic dermatitis, post-inflammatory hyperpigmentation, cataract, ochronosis, among others, encouraged the search for new whitening principles.

PURPOSE OF THE INVENTION

Therefore, the purpose of this invention is to supply a skin-whitener, adding efficacy and safety criteria through a complex containing four de-pigmenting agents performing in synergic manner.

In order to reach such goal, this invention refers to a composition for cosmetic application providing skin-whitening action, as well as the preparation process of said composition. In a first aspect hereof, a cosmetic composition is supplied, comprehending four active ingredients: Undecylenoyl phenylalanine, alpha-arbutin, kojic acid and *brassica napus* extract. In a second aspect hereof, a preparation process of the skin depigmenting composition is supplied.

DETAILED DESCRIPTION OF THE INVENTION

The conception of this purpose of the invention was based on the first main steps of melanogenesis cascade:
Inhibition of the activity of tyrosinase enxyme;
Reduction of the biosynthesis of melanin and precursors;
Inhibition of the genic expression and activity of ET-1: inhibition of the dendricity of melanocytes;
Reduction in the genic expression and activity of PAR-2: inhibition of the transference of formed melanin to adjacent keratinocytes;
Promotion of cellular proliferation, resulting in an acceleration in the elimination of melanin already deposited on skin.

This invention, based on the steps of melanogenesis cascade for dermatologic treatment, comprehends four active, skin-whitening, components, namely: Undecylenoyl phenylalanine, alpha-arbutin, kojic acid and *brassica napus* extract. This combination is capable of drastically reducing skin hyperpigmentation, in a fast, safe and long-lasting manner, compare to the description of the state of the technique. The active components contained in the purpose of the invention are already known as depigmenting agents, as we may notice in the U.S. patent application Ser. No. 12/440,707, called "PIGMENTATION-REGULATING COMPOUNDS" deposited by LIPOTEC, S. A, which originated from PCT/ES2008/000230 deposited on Apr. 11, 2008. This application describes a composition for the treatment, care and/or cleaning of skin, hair and/or nails, preferably to attenuate the pigmentation degree of skin, hair or for the treatment of stains on nails or photo protection of skin, hair and nails. U.S. patent application Ser. No. 12/440,707 protects a pharmaceutical or cosmetic composition containing a whitening active ingredient or a depigmenting agent selected from a large list of substances exercising such function. This list of whitening active ingredients and depigmenting agents contains undecylenoyl phenylalanine, alpha-arbutin, kojic acid and *brassica napus* extract. However, the use thereof is made individually of the lists proposed, rather than combined in the composition described and claimed in U.S. Ser. No. 12/440,707. The association of the 4 synergic actives, undecylenoyl phenylalanine, alpha-arbutin, kojic acid and *brassica napus* extract, in a depigmenting cosmetic composition with the characteristics hereof is not, therefore, suggested to us in the state of the technique.

The main mechanisms through which depigmenting actives perform are:
1) Selectivity or cytotoxicity, destroying or decharacterizing melanocytes;
2) Antioxidant action;
3) Interference with the biosynthesis of melanin and precursors;
4) Inactivation or prevention of biosynthesis of tyrosinase enzyme;
5) Interference in the transportation of the melanin granulomas within melanosomes to adjacent keratinocytes. Such interference occurs through the inhibition of the PAR-2 receptor (protease activated receptor-2);
6) Through the inhibition of melanocytes dendricity, i.e., the capacity of the active of inhibiting ET-1 (endothelin-1);
7) Through the change (reduction capacity) of brown melanin present in melanosomes (oxidized form) to a clearer color (reduced form);
8) Through the reduction of melanogenic hormones production, Despite the broad knowledge involving the complex melogenesis cascade and the formation of hypermelanoses, few dermacosmetic products in the market are able to reach the desired therapeutic success, adding efficacy and safety criteria in the same formulation. In the attempt of fulfilling this need, the depigmenting cosmetic composition hereof was developed. The combination of the 4 synergic actives, object hereof, grants this cosmetic composition a triple oxidizing action, capable of reducing the formation of three different forms of free radicals: oxygenated, nitrogenized and carbonated, all resulting of the degenerative oxidizing cascade. The compositions existing in the state of the technique are not capable of fully blocking the oxidative cascade while the depigmenting composition hereof, containing the combination of the 4 synergic actives has a complete triple antioxidant system. The depigmenting composition hereof acts directly on the PAR-2, receptor responsible for the receipt of melanin contained in the melanosomes by the keratinocytes, having the intrinsic capacity of reducing the transference and distribution of oxidized pigments to the adjacent skin layers, providing a uniformization in skin tone and reducing hyperpigmentation. This innovative combination of the 4 synergic actives generates a safe composition for correction of pigmentary disorders, once it promotes melanin reduction, reduces the skin pigmentation level and promotes an improvement in the general skin quality, compared to hyperpigmentation. The amount of active ingredients in the composition hereof comprehends 0.01 to 2.0% of undecylenoyl phenylalanine, 0.2 to 2.0% of alpha-arbutin, 1.0 to 3.0% of kojic acid and 1.0 to 3.0% of *brassica napus* extract, in weight. The first skin-whitening agent constituting this invention is called undecylenoyl phenylalanine, CAS No. 175357-18-3, consisting in an antagonist of the melanocyte or melanotropin stimulating hormone. Thus, the following steps of melanin synthesis are inhibited: Affinity for the melanotropin MC1R receptor, inhibition of adenylate enzyme, cycle-eduction of intracellular content of cyclic AMP, inhibition of the kinase A protein and inhibition of melanogenesis. The active undecylenoyl phenylalanine effectively inhibits the activity of tyrosinase, acting as a false substrate to such enzyme. The second skin whitening agent constituting this invention is the active alpha-arbutin, CAS No. 84380-01-8, a pure active ingredient, hydro soluble and biosynthetic. The whitening effect of alpha-arbutin is due to the capacity of acting as a substrate of tyrosinase, inhibiting it. This active has the properties of minimizing the existing stains and reducing the tanning degree of skin after UV exposure. The third skin-whitening agent constituting this invention is kojic acid, CAS No. 501-30-4, a natural substance, produced by various fungi and bacteria, hydro soluble and odorless. Among its properties are the antimicrobial and chelating action of copper ions, and the latter is responsible for the inactivation of tyrosinase and, as a consequence, by the inhibiting action on melanin formation. It is a powerful non-cytotoxic depigmenting substance, with the benefit of having soft action on skin, without causing irritation and photo sensitization on the used, allowing the use during the day. Kojic acid induces the reduction of eumelanin and of its key precursor, inhibits tyrosinase and absorbs ultraviolet rays.

The fourth skin-whitening agent constituting this invention is *brassica napus* extract, CAS No. 89958-03-2. It consists in the extract of Brassicaceae, which hydrolyzed and fermented proteins are responsible for the whitening effect. This substance presents two main applications: Reducing the appearance of senile stains and skin-whitening in general. It acts inhibiting the activity of tyrosinase enzyme, reducing, therefore, the formation of melanin on skin. In addition to the active ingredients, the depigmenting composition comprehends water, the emollient, the emulsifier, the humectant, the thickener, the hydrating, the antioxidizer, the tamponing and the sequestrant. Preferred emollients are diisopropyl adipate; Shea butter oleyl esters and caprylhydroxamic acid/caprylyl glycol/glycerin. Preferred emulsifiers are: Behenyl alcohol/glyceryl stearate/lecithin/glycine soja sterols; Glyceryl stearate/cetearyl alcohol/stearic acid/sodium cocoyl glutamate and sodium acrylates copolymer/hydrogenated polyisobutene/phospholipids/polyglyceryl-10 stearate/*helianthus annuus* seed oil. Preferred humectant is glycerin. The most preferred thickener is PEG-14M. The preferred hydrating is saccharide isomerate. The preferred antioxidant is canola oil. Preferred tamponing ingredients are sodium citrate and citric acid. The most preferred sequestrant isdisodium edta.

The formulation preparation process is comprised of the following steps:

Beginning in the aqueous phase at the temperature of 22-38° C., wherein the vehicle, the sequestrant, the tamponings and the thickener are homogenized, with temperature adjustment at 60-70° C.;

Then, the preparation of oily phase occurs, wherein the antioxidizer, the emollients and emulsifiers are agitated until they reach a temperature of 60-70° C., when undecylenoyl phenylalanine, first whitening agent, is added. It is homogenized and adjusted to the temperature of 80-85° C.;

The oily phase is added on the aqueous phase, under vacuum. Homogenization is maintained and it adjusts to the temperature of 65-70° C. In this step, micelle is formed, wherein the first whitening agent is in the internal micelle phase;

In an auxiliary tank, alpha-arbutin, second whitening agent, is solubilized in water at a temperature of 60-70° C. and added to emulsion. Thus, the second whitening agent is in the external micelle phase. Homogenization is maintained and it adjusts to the temperature of 22-38° C.;

In an auxiliary vial, kojic acid is dispersed, the third whitening agent, and glycerin; added to emulsion. Thus, the third whitening agent remains in the external micelle phase;

One by one, the emollient, hydrating and *brassica napus* extract—fourth whitening agent—are added to the emulsion. It is homogenized.

The fourth whitening agent remains in the external micelle phase.

Therefore, in this preparation process, the active whitening agents are both in the internal and external micelle phase. The parameters of this composition must include pH between 3.0 and 5.0, uniform emulsion, slightly yellowish to yellowish, with characteristic odor and free of foreign particles.

It must be evident to those skilled in the technique that this invention may be configured in many other specific manners without deviating from the spirit or scope of the invention. Particularly, one must comprehend that the invention may be configured as described.

Therefore, the examples and embodiments shall be considered illustrative, rather than restrictive, and the invention must not be limited to the details supplied herein, but may be modified within the scope and equivalence of the claims attached.

The invention claimed is:

1. A method of preparing a depigmenting cosmetic composition, comprising the steps of:
    A) providing an aqueous phase, wherein a vehicle, a sequestrant, a tamponing ingredient, and a thickener are homogenized;
    B) providing an oily phase comprising an antioxidizer, one or more emollients, and one or more emulsifiers, followed by addition of a first whitening agent to the oily phase and homogenization, wherein the first whitening agent is undecylenoyl phenylalanine;
    C) adding the oily phase to the aqueous phase under vacuum, thereby forming an emulsion comprising an internal micelle phase and an external micelle phase, wherein homogenization is maintained, and wherein the first whitening agent is in the internal micelle phase;
    D) adding a first solution comprising a second whitening agent solubilized in water to the emulsion formed in step C, wherein homogenization is maintained, wherein the second whitening agent is in the external micelle phase, and wherein the second whitening agent is alpha-arbutin, to form an emulsion with an internal and external micelle phase;
    E) adding a second solution comprising a third whitening agent dissolved in glycerin to the emulsion formed in step D, wherein the third whitening agent is in the external micelle phase, and wherein the third whitening agent is kojic acid to form an emulsion with an internal and external micelle phase; and
    F) adding an emollient followed by a fourth whitening agent to the emulsion formed in step E, followed by homogenization, thereby forming the depigmenting cosmetic composition, wherein the fourth whitening agent is in the external micelle phase, and wherein the fourth whitening agent is *brassica napus* extract.

2. The method of claim 1, wherein the depigmenting cosmetic composition has a pH between 3.0 and 5.0.

3. The method of claim 1, wherein the depigmenting cosmetic composition is a uniform emulsion.

4. The method of claim 1, wherein the vehicle is water.

5. The method of claim 4, wherein the sequestrant is disodium EDTA.

6. The method of claim 5, wherein the tamponing ingredient is selected from the group consisting of citric acid and sodium citrate.

7. The method of claim 1, wherein in step A, the aqueous phase is provided at a temperature between 22 and 38° C.

8. The method of claim 7, wherein step A further comprises adjusting the temperature of the aqueous phase to between 60 and 70° C.

9. The method of claim 8, wherein in step B, the oily phase is provided at a temperature between 60 and 70° C.

10. The method of claim 9, wherein step B further comprises adjusting the temperature of the oily phase to between 80 and 85° C.

11. The method of claim 10, wherein in step C, the temperature of the emulsion is adjusted to between 65 and 70° C.

12. The method of claim 11, wherein in step D, the temperature of the first solution is at a temperature between 60 and 70° C.

13. The method of claim 12, wherein in step D, following addition of the first solution, the temperature is adjusted to between 22 and 38° C.

14. The method of claim 1, wherein the depigmenting cosmetic composition comprises between 0.01 to 2.0% undecylenoyl phenylalanine by weight, between 0.02 to 2.0% alpha-arbutin by weight, between 1.0 to 3.0% kojic acid by weight, and between 1.0 to 3.0% *brassica napus* extract by weight, of the total weight of the depigmenting cosmetic composition.

* * * * *